US006994975B2

(12) United States Patent
Gatti et al.

(10) Patent No.: US 6,994,975 B2
(45) Date of Patent: *Feb. 7, 2006

(54) EXPRESSION AND PURIFICATION OF ATM PROTEIN USING VACCINIA VIRUS

(75) Inventors: Richard A. Gatti, Sherman Oaks, CA (US); Helen H. Chun, Woodland Hills, CA (US); David J. Rawlings, Seattle, WA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 134 days.

(21) Appl. No.: 10/042,775

(22) Filed: Jan. 8, 2002

(65) Prior Publication Data

US 2003/0129651 A1    Jul. 10, 2003

(51) Int. Cl.
G01N 33/53 (2006.01)
C12P 21/06 (2006.01)
C12N 15/00 (2006.01)
C12N 5/08 (2006.01)
A61K 39/12 (2006.01)

(52) U.S. Cl. .................... 435/7.1; 435/69.1; 435/320.1; 435/372; 435/367; 435/456; 435/183; 424/9.34; 424/93.21; 424/199.1; 530/350

(58) Field of Classification Search ............... 435/69.1, 435/70, 320.1, 232.1, 71.1, 72.3, 325, 7.1, 435/456, 183, 367, 372; 424/199.1, 208.1, 424/188.1, 93.21, 9.34; 530/350
See application file for complete search history.

(56) References Cited

U.S. PATENT DOCUMENTS

| 5,858,661 A | 1/1999 | Shiloh |
| 5,955,279 A | 9/1999 | Gatti et al. |
| 6,211,336 B1 | 4/2001 | Shiloh et al. |
| 6,265,158 B1 | 7/2001 | Shiloh |
| 6,387,640 B1 * | 5/2002 | Kastan et al. .................. 435/15 |

OTHER PUBLICATIONS

Zhang et al. Isolation of full-length ATM cDNA and correction of the ataxia-telangiectasia cellular phenotype. Jul. 1997, vol. 94, pp 8021-8026.*
Rappold et al. Tumor Suppressor p53 Binding Protein 1 (53BP1) Is Involved in DNA Damage-signaling Pathways. Apr. 2001, vol. 153, No. 3, pp 613-620.*
Chakrabarti et al. Compact, Synthetic, Vaccinia Virus Early/Late Promoter for Protein Expression. Biotechniques. vol. 23(6) (1997) pp 109-1097.*
Gately et al. Characterization of ATM Expression, Localization, and Associated DNA dependent Protein Kinase Activity. Molecular Biology of the Cell, vol. 9 (1998) pp 2361-2374.*
Smith et al. Purification and DNA binding properties of the ataxia-telangiectasia gene product ATM. PNAS vol. 96, (1999) pp 11134-11139.*
Moss, B. Poxviridae: The Viruses and Their Replication, 1996, Raven Publishers, Chapter 34, pp 1165.*
S. Banin, L. Moyal, S.-Y. Shieh, Y. Taya, C.W. Anderson. L. Chessa, N.I. Smorodinsky, C. Prives, Y. Reiss, Y. Shiloh, Y. Ziv (1998) Enhanced Phosphorylation of p53 by ATM in Response to DNA Damage, *Science*, 281: 1674-1677.
C.E. Canman, D. Lim, K.A. Cimprich, Y. Taya, K. Tamai, K. Sakaguchi, E. Appella, M. B. Kastan, J.D. Siliciano (1998) Activation of the ATM Kinase by Ionizing Radiation and Phosphorylation of p53, *Science*, 281: 1677-1679.
D.W. Chan, S-C. Son, W. Block, R. Ye, K.K. Khanna, M.S. Wold, P. Douglas, A.A. Goodarzi, J. Petley, Y. Taya, M.F. Lavin, S.P. Lees-Miller (2000) Purification and Characterization of ATM from Human Placenta, *Journal of Biological Chemistry*, 275:7803-7810.
R. A. Gatti (2001) *Ataxia-Telangiectasia, Ch. 29*, in, *Metabolic and Molecular Bases of Inherited Disease*, $8^{th}$ Ed., Scriver et al. Eds, pp. 705-732.
M. Platzer, G. Rotman, D. Bauer, T. Uzlei, K. Savitsky, A. Bar-Shira, S. Gilad, Y. Shiloh, A. Rosenthal (1997) Ataxia-Telangiectasia Locus: Sequence Analysis of 184 kb of Human Genomic DNA Containing the Entire ATM Gene, *Genome Research* 7:592-605.
N. Rhodes, T. M. Gilmer, T. J. Lansing, (2001) Expression and Purification of Active Recombinant ATM Protein from Translently Transfected Mammalian Cells, *Protein Expression and Purification* 22:462-466.
K. Savitsky, S. Sfez, D.A. Tagle, Y.Ziv, A. Sartiel, F.S. Collins, Y. Shiloh, G. Rotman (1995) The Complete Sequence of the Coding Region of the ATM Gene Reveals Similarity to Cell Cycle Regulators in Different Species, *Human Molecular Genetics* 4:2025-2032.
S.P. Scott, N. Zhang, K.K. Khanna, A. Khromykh, K. Hobson, D. Watters, M. F. Lavin (1998) Cloning and Expression of the Ataxia-Telangiectasia Gene in Baculovirus, *Biochemical and Biophysical Research Communications* 245:144-148, Article No. RC 988137.

(Continued)

*Primary Examiner*—Terry McKelvey
*Assistant Examiner*—Maria Marvich
(74) *Attorney, Agent, or Firm*—Knobbe Martens Olson & Bear, LLP

(57) ABSTRACT

The present disclosure concerns methods for recombinantly producing functional ataxia-telangiectasia (ATM) protein, methods for isolating recombinant functional ATM protein, and uses of ATM protein. In particular, a method is disclosed for using a vaccinia virus vector to express ATM, and using immunoprecipitation or affinity tagging to isolate recombinant ATM.

16 Claims, 3 Drawing Sheets

OTHER PUBLICATIONS

T. Shafman, K.K. Khanna, P. Kedar, P. Spring, S. Kozlov, T. Yen, K. Hobson, M. Gatei, N. Zhang, D. Watters, M. Egerton, J. Shiloh, S. Kharbanda, D. Kufe, M. F. Lavin, (1997) Interaction Between ATM Protein and c-Abl in Response to DNA Damage, *Nature* 387:520-523.

G. C. M. Smith, R. B. Cary, N.D. Lakin, B.C. Hann, S.H. Teo, D.J. Chen, S. P. Jackson (1999) Purification and DNA Binding Properties of the Ataxia-Telangiectasia Gene Product ATM, *Proc. Natl. Acad. Sci.* (USA) 96:11134-11139.

Y. Ziv, A. Bar-Shira, I. Pecker, P. Russell, T. J. Jorgensen, I. Tsarfati, Y. Shiloh, (1997) Recombinant ATM protein Complements the Cellular A-T Phenotype, *Oncogene* 15:159-167.

GenBank Accession U82828, Homo Sapiens Ataxia Telangiectasia (ATM) Gene, complete cds. Aug. 7, 1997.

GenBank Accession U33841, Human Ataxia Telangiectasia (ATM) mRNA, complete cds. Nov. 29, 1995.

* cited by examiner

Figure 3. Silver Stain of Purified ATM Protein
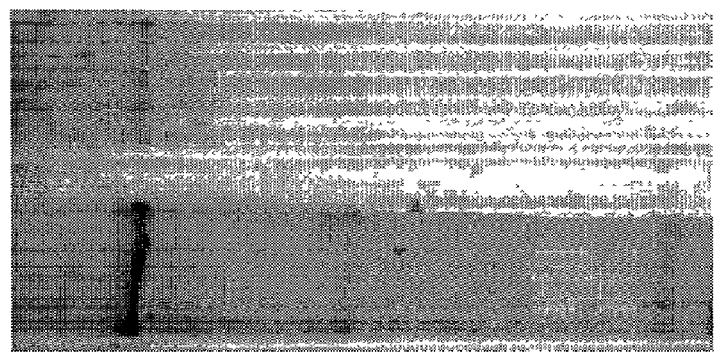
ATM →
Approximate concentration:   1ug       0.2ug

EXPRESSION AND PURIFICATION OF ATM PROTEIN USING VACCINIA VIRUS

GOVERNMENTAL SUPPORT

This invention was made with Government support by Grant No. NS35322, awarded by the National Institutes of Health. The Government has certain rights in this invention.

FIELD OF THE INVENTION

The present invention relates to expression of functional recombinant ATM protein. In particular, the disclosure describes construction of a recombinant vaccinia virus expressing functional ATM, purification of the protein from infected HeLa cells, and demonstration of activity of the purified protein by means of in vivo and in vitro assays.

BACKGROUND OF THE INVENTION

Ataxia-telangiectasia (A-T) is a genetic recessive disorder that affects 1 in 40,000 to 100,000 births. Patients are affected by a large range of symptoms including telangiectasae (dilation of blood vessels) on the eyes, face, and shoulders, ataxia (loss of balance), neurodegeneration, cerebellar degeneration, ocular telangiectasia, radiosensitivity, cancer predisposition, immunodeficiency, and premature aging. A-T cells display cell cycle checkpoint defects, chromosomal instability, and sensitivity to ionizing radiation.

The A-T gene, cloned by positional cloning (Savitsky et al (1995) Hum. Mol. Genet. 4: 2025–2032) encodes a 350 kDa protein kinase known as "ataxia-telangiectasia, mutated" (ATM) involved with the DNA double-stranded break response mechanism and initiation of repair, which are events responsible for maintaining the genomic integrity of the cell. Activation of ATM has effects on multiple signal transduction pathways related to cell cycle checkpoints and DNA damage repair. Complete genomic sequence (184 kb) of the A-T gene, also known as the ATM gene, is disclosed at GenBank Accession No. U82828 (Platzer et al. (1997) Genome Res. 7 (6), 592–605). ATM mRNA is disclosed at GenBank Accession No. U33841 (Savitsky et al (1995) Hum. Mol. Genet. 4: 2025–2032). Cloning, sequences, and organization of the A-T gene are disclosed, inter alia, in U.S. Pat. Nos. 6,265,158, 6,211,336 and 5,858,661 to Shiloh et al., and mutations in the A-T gene are disclosed in U.S. Pat. No. 5,955,279 to Gatti et al.

ATM is a serine/threonine kinase that targets many substrates including p53, RPA, MDM2, NBS1, Chk2, RPA, BRCA1, and other substrates that are postulated but currently unknown. (Gatti et al., (2001) in Metabolic and Molecular Bases of Inherited Disease, 8$^{th}$ Ed, Scriver et al. Eds, pp 705–732) ATM is a member of a family of large kinases containing a C-terminal end homologous to the phosphatidylinositol 3-kinase domain. These proteins play a role in cell cycle checkpoint or DNA damage repair. Other proteins in this family include Rad 3, Mec1p, Mei-41, Rad 50, Tel1 and DNA-PK.

Many aspects of ATM function have been elucidated, but little is known about the structure due to difficulties in isolating ATM. Only a few domains have been identified based on protein homology (Savitsky, K., et al. (1995) Human Molecular Genetics 4: 2025–2032) and biochemical activity (Shafinan, T., et al. (1997) Nature 386: 520–523; Banin, S., et al. (1998) Science 281:1674–1677; Canman, C., et al. (1998) Science 281: 1677–1679).

Overexpression of ATM has been difficult to accomplish due to the instability of the cDNA and the large protein size. Baculovirus expression and protein purification has been attempted (Scott et al. (1998) Biochem Biophys Res Comm 245:144–148) but a high protein yield was difficult to obtain. When ATM was overexpressed in insect cells, only a fraction of recombinant protein was found in the soluble portions of cell preparations, and the majority of the protein was associated with cellular membranes (Ziv et al. (1997) Oncogene 15, 159–167). In 100 ml of infected insect cells, only 20 ng of ATM was produced (Scott et al. (1998) Biochem Biophys Res Comm 245: 144–148), whereas expression of other recombinant proteins often results in recovery of milligram amounts of protein.

Purification of endogenous ATM by conventional biochemical methods has resulted in extremely low yields of purified protein. Smith and colleagues purified ATM from 50 ug of HeLa cell nuclear extract using a series of chromatography columns (Smith et al. (1999) Proc Natl Acad Sci USA 96: 11134–11139). A double-stranded DNA column was used as the last purification step resulting in a homogenous elution. Atomic force microscopy, used to visualize biological interactions, was used to analyze purified ATM and showed that ATM exists as monomers and tetramers. (Smith et al., (1999) Proc Natl Acad Sci USA 96: 11134–11139)

Chan et al. purified endogenous ATM from human placenta using various biochemical chromatographic steps, resulting in approximately 2 ug of ATM protein from 300 grams of placenta tissue, whereas 500 ug of DNA-protein kinase catalytic subunit (DNA-PKcs) protein was isolated from the same tissue. (Chan et al (2000) Jnl Biol Chem 275: 7803–7810) Rhodes et al. purified FLAG-tagged ATM by transiently transfecting an expression construct in HEK 293T cells and isolating ATM using an anti-FLAG affinity column. (Rhodes et al. (2001) Prot Expression and Purif 22: 462–466) Rhodes et al. were able to purify only 1 ug of ATM protein from a 225 cm$^2$ flask that had been seeded with $8 \times 10^6$ uninfected cells and incubated for overnight prior to transfection, and then incubated for another 24 hours after transfection. Thus, the protein recovery reported by Rhodes et al. appeared to be about 1 ug ATM protein from at least $8 \times 10^6$ cells, and relative yield may be even lower if cell division occurred during incubation such that substantially more cells were used for purification. (Rhodes et al. (2001) Prot Expression and Purif 22: 462–466)

A DNA requirement in ATM activation has been reported, but has been disputed. Banin et al and Canman et al. reported ATM kinase activity against p53 substrate, where the activity was independent of DNA. (Banin et al. (1998) Science 281: 1674–1677; Canman et al. (1998) Science 281: 1677–1679) Chan et al. determined that ATM activity and was manganese-dependent and DNA-independent, except when ATM was phosphorylating RPA, in which case DNA was required. (Chan et al (2000) Jnl Biol Chem 275: 7803–7810) Smith et al. used DNA-iron oxide particles as their final purification step to isolate ATM from HeLa cells. (Smith et al. (1999) Proc Natl Acad Sci USA 96: 11134–11139) They reported an increase of kinase activity in the presence of sheared DNA. Using atomic force microscopy, Smith et al. (1999) showed ATM preferentially localizing to ends of DNA double strand gaps, providing some evidence of a protein-DNA interaction. (Smith et al. (1999) Proc Natl Acad Sci USA 96: 11134–11139)

SUMMARY OF THE INVENTION

The present invention provides expression and purification of functional ATM protein, and further provides substantially purified ATM protein and uses thereof.

The present invention provides a method for recombinantly producing functional ataxia-telangiectasia (ATM) protein, using a viral vector containing a gene encoding the ATM protein operably linked to promoter, then infecting mammalian cells with the viral vector such that infected cells produce the ATM protein, and isolating the ATM protein produced by the infected mammalian cells. The viral vector containing a gene encoding the ATM protein may be operably linked to a promoter that may be a vaccinia viral vector. For this method, the viral vector containing a gene encoding the ATM protein operably linked to promoter may be the pSCAT vector. The promoter may be a synthetic early/late viral promoter. The mammalian cell that is infected with viral vector may be HeLa cell. For this method, ATM protein can be isolated by binding an anti-ATM antibody to the ATM protein. The ATM protein produced by this method may be modified to contain a FLAG epitope, and ATM protein can be isolated by binding an anti-FLAG antibody to the FLAG-tagged ATM protein.

The method disclosed herein provides for production of functional ATM protein that can be isolated with a yield of greater than 2 ug substantially purified ATM protein per 300 grams fresh weight of host cells or host tissue.

The present invention further provides a method for recombinantly producing a high yield of functional ataxia-telangiectasia (ATM) protein, using a viral vector containing a gene encoding the ATM protein operably linked to promoter, infecting mammalian cells with the recombinant viral vector, wherein the mammalian cells produce the ATM protein, and by isolating the ATM protein produced by the infected mammalian cells. High yield of functional ATM protein is considered to be greater than 2 ug substantially purified ATM protein from 300 grams fresh weight of host cells or host tissue. High yield can be achieved by isolating ATM protein by binding an anti-ATM antibody to the ATM protein.

BRIEF DESCRIPTION OF THE DRAWINGS

FIG. 3. Silver stained SDS-PAGE of purified ATM protein. 1 ug (right lane) and 200 ng (left lane) of purified ATM was electrophoresed on a denaturing polyacrylamide gel, followed by silver staining for visualization. Full-length ATM is the major protein in both lanes, which contained slight traces of smaller protein fragments at much lower concentrations.

DETAILED DESCRIPTION OF THE PREFERRED EMBODIMENT

Figure 1:
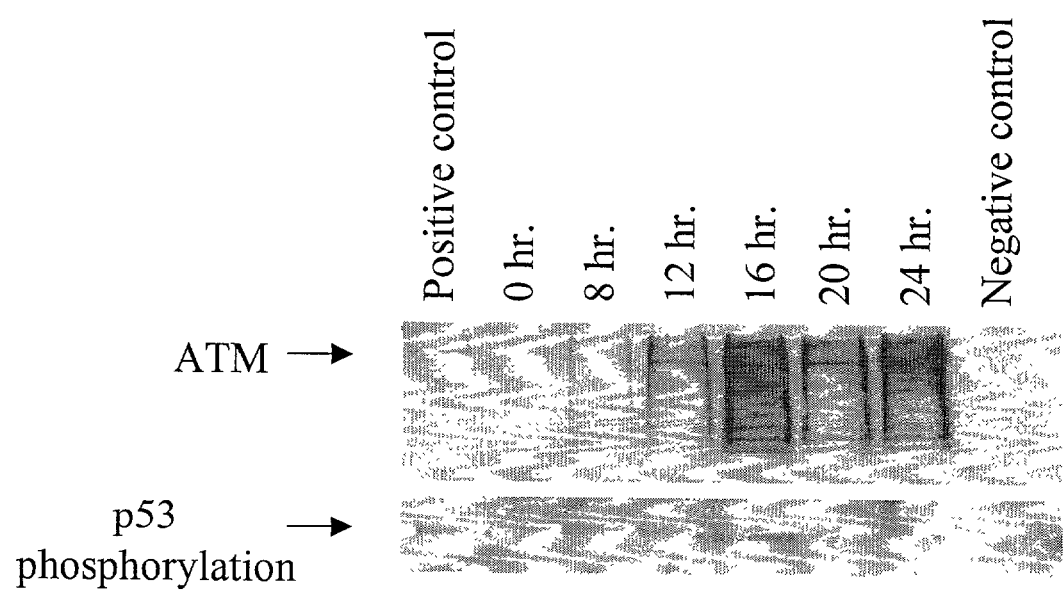
FIG. 1. Expression and activity of recombinant ATM. Upper panel: Western blot analysis of ATM protein expression in L3 cells infected with ATM-expressing vaccinia virus. At indicated timepoints, cells were irradiated with 2 Gy gamma radiation, lysed, and sonicated after 15 minutes. Using anti-ATM antibody on a Western blot of cell lysate, protein was detected as early as 8 hours after infection. Lower panel: Western blot analysis indicating ATM kinase activity after IR treatment, using anti-phospho-p53-serine-15 antibody to detect ATM phosphorylation of p53 at serine 15. Activity correlated with the presence of ATM expression. In the "negative control" sample, L3 cells were infected with vaccinia virus expressing a different protein other than ATM, and no ATM expression (upper panel) or activity (lower panel) was found in those cells.

The present invention provides expression of functional ATM protein, purification of functional ATM, and further provides substantially purified ATM protein and uses thereof. The ATM protein plays an important role in detecting double strand DNA breaks produced by cellular metabolism or environmental agents, but biochemical studies of ATM function have been hampered by the lack of sufficient amounts of purified functional protein. Aspects of the present invention address this problem by providing successful expression and purification of functional ATM protein, as well as compositions containing substantially purified ATM protein.

One aspect of the present invention provides an expression system that produces a high yield of functional ATM protein, where a high yield of functional ATM protein is a yield greater than 2 ug substantially pure ATM protein per 300 grams fresh weight of host cells or host tissue.

Preferably, a host cell is infected with a recombinant viral system that expresses ATM. More preferably, mammalian cells and even more preferably, human cells, are infected with a recombinant viral system that expresses ATM.

In accordance with one aspect, a recombinant viral expression system is provided. In one embodiment, a recombinant expression system using vaccinia virus containing ATM coding sequence produces a high yield of ATM protein in host cells. Preferably, a mammalian host cell is infected with the recombinant ATM viral expression system; more preferably a human host cell is infected. In a more preferred embodiment, an expression system using vaccinia virus containing ATM coding sequence fused to coding sequence for the 8-amino-acid FLAG peptide is used to produce FLAG-tagged ATM protein in HeLa cells. In another preferred embodiment, an expression system using vaccinia virus containing ATM coding sequence fused to coding sequence for a 6-amino acid hexahistidine peptide and fused to coding sequence for 8-amino acid FLAG peptide is used to produce FLAG-and-His-tagged ATM protein in HeLa cells.

Another aspect of the present invention provides construction of a recombinant vaccinia virus expressing ATM protein. In a preferred embodiment, recombinant vaccinia virus containing ATM coding sequence can be used to infect cells to produce large amounts of functional FLAG tagged ATM protein in HeLa cells. In another preferred embodiment, host cells infected with recombinant ATM-expressing virus overproduce ATM.

Yet another aspect of the invention provides determination of functional ATM activity. In a preferred embodiment, in vivo assays show a regain of ATM function in an ATM deficient cell line infected by recombinant vaccinia virus expressing ATM protein.

Another aspect of the present invention provides methods for purification of recombinant functional ATM protein and recovery of substantially purified recombinant ATM produced in accordance with the methods of the present invention. In a preferred embodiment, recombinant ATM protein is purified using immunoprecipitation or an antibody-coupled affinity resin using at least one anti-ATM antibody.

In another preferred embodiment, recombinant FLAG-tagged ATM protein is purified using a FLAG affinity resin.

In another aspect of the present invention, in vitro and in vivo assays of substantially purified recombinant ATM show ATM-specific kinase activity towards substrates including p53 and PHAS-1, as well as autophosphorylation. In a preferred embodiment, in vitro kinase assays using substantially purified ATM protein and p53 and PHAS-1 as target proteins, provide evidence of ATM specific kinase activity after isolation. In another preferred embodiment, p53 phosphorylation by recombinant ATM protein is dependent on the presence of sheared double stranded DNA, while PHAS-1 phosphorylation and ATM autophosphorylation are DNA independent.

Other embodiments include construction of other suitable viruses capable of expression the entire ATM protein or fragments thereof, including but not limited to variola virus, Sindbis virus, or baculovirus.

ATM Expression by Vaccinia Virus

Construction of Recombinant ATM-Expressing Vaccinia Virus

Since cellular ATM levels are inherently low, one aspect of the present invention provides expression of a recombinant viral system that expresses ATM as a method to produce a high yield of ATM protein. In a particularly preferred embodiment, vaccinia virus is used for expression of ATM protein, and in an even more preferred embodiment, vaccinia virus is used for overexpression of ATM protein. The vaccinia virus, a member of the variola virus family, has several advantages as an expression system. The vaccinia viral genome can incorporate and express large pieces of foreign DNA making the system a potential technique in protein overexpression and purification of ATM. Additional advantages of the vaccinia virus include infectability of a wide host range, cytoplasmic transcription, high expression levels, and proper processing and transport. In one particularly advantageous aspect of the present invention, cytoplasmic transcription provides a distinct advantage since transcription occurs outside of the host nucleus, such that splicing of viral transcripts is not required and the risk of altered splicing is avoided.

In a preferred embodiment, full-length human ATM cDNA (GenBank Accession No. U33841) was inserted into the pSC65 vaccinia vector (Chakrabarti et al (1997) *Biotechniques* 23: 1094–1097) containing a synthetic "early/late promoter" having both early and late gene promoters such that an insert is expressed throughout the virus life cycle, and also containing the tk (thymidine kinase) gene. Insertion of full-length ATM into pSC65 produced the pSCAT expression vector, which was transfected into CV-1 tk-cells from a monkey kidney cell line that were simultaneously transfected with the WR strain of vaccinia virus (WR strain: ATCC VR 1354), and ATM-encoding polynucleotide was incorporated into the viral genome at the tk gene locus, preferably by homologous recombination. Double selection was performed to isolate a single population of recombinant virus. For double selection, ATM was inserted into the viral genome by homologous recombination at the tk locus. The first selection involved a negative tk selection to determine if homologous recombination took place between the vaccinia vector and the viral genome, as a cell expressing thymidine kinase gene will be killed in the presence of bromodeoxyuridine (BrdU). The CV-1 cell line lacks thymidine kinase (tk-) and the vector has the tk gene. In this embodiment, ATM is inserted into the tk gene, making tk nonfunctional. After introduction of ATM into the viral genome, recombinant viruses with successful homologous recombination are identified by having a tk-phenotype. A second selection step uses color, preferably lacZ, to select for transfected tk-cells.

Infection of Host Cells with Recombinant ATM-Expressing Vaccinia Virus

In accordance with another aspect of the present invention, recombinant ATM-expressing vaccinia virus is recovered from infected cells and used to infect other host cells. In a particularly preferred embodiment, recombinant ATM-expressing vaccinia virus was used to infect HeLa cells (ATCC Accession No CCL2.2)

In accordance with another aspect of the present invention, a stock of cells is infected with recombinant ATM-expressing vaccinia virus, for uses including but not limited to maintaining or propagating stocks of infected cells for future use and for preparation of amplification stock for purification or measurements of ATM protein. In a preferred embodiment, CV-1 cells are infected with recombinant ATM-expressing vaccinia virus, incubated for about 48 hours, and cells are harvested. Infected cells may be stored, and/or may be used in subsequence purification steps.

In another embodiment, expression and function of ATM was examined at various timepoints over a timecourse of up to 48 hours by infecting an ATM deficient human lymphoblastoid cell line with ATM-expressing virus a vector expressing ATM for about 24 to 32 hours. In a preferred embodiment, ATM deficient human lymphoblastoid cell line L3 was used. L3 cells have a homozygous 103 C-to-T mutation, resulting in no detectable expression of ATM protein. In one embodiment, $1\times10^6$ L3 cells were infected by ATM expressing virus and cells were collected every 4 hours. The cell sample collected at each timepoint was exposed to 2 Gy gamma radiation to activate ATM, and the cells were lysed after 15 minutes, allowing for ATM specific phosphorylation of L3 cells' p53 at serine 15. Immunoblot analysis show that ATM levels increased after 4 hours, peaking at 16 hours, and slightly decreased at later timepoints (FIG. 1, upper panel). A negative control lane shows that ATM expression was not seen when L3 cells were infected with another recombinant virus expressing a different protein, indicating that the presence of ATM protein was due to viral infection with ATM-expressing vaccinia. In another embodiment, ATM expression was not seen in uninfected L3 cells, indicating that the presence of ATM protein was due to viral infection with ATM-expressing vaccinia.

In another embodiment, lysates from cells infected with ATM-expressing virus were incubated with anti-phospho-p53-serine-15 antibodies to detect phosphorylation of p53 at the serine 15 position by ATM. ATM specific phosphorylation was observed at 8 hours after infection and increased until a peak at 16 hours (FIG. 1, lower panel). After 16 hours, phosphorylated p53 levels decreased. Phosphorylation of p53 in L3 cells signified a regain of function in an otherwise ATM-deficient cell. In this embodiment, the phosphorylation levels suggest overexpression of a functional ATM protein by ATM-expressing vaccinia virus.

Promoters suitable for use in accordance with the present invention include promoters which will drive expression in a chosen viral vector, and which will be recognized by the viral machinery responsible for driving expression, where promoter drives expression throughout the life cycle of the virus. Such promoters may be isolated directly from an organism or may be a synthetic promoter construct and may include, but are not limited to, a synthetic early/late promoter of vaccinia.

In accordance with the invention, standard molecular biology techniques may be used which are within the level of skill in the art. Such techniques are fully described in the literature. See for example; Sambrook et al (1989) *Molecular Cloning; a laboratory manual*; Hames and Glover (1985–1997) DNA *Cloning: a practical approach*, Volumes I–IV (second edition).

Purification of ATM

Another aspect of the present invention concerns purification of recombinant ATM produced in accordance with the methods of the invention. One skilled in the art can purify ATM using standard techniques for protein purification. One skilled in the art can determine the level of purity desired for a specific purpose, and can develop purification strategies to achieve the desired level of purity. Substantially pure whole ATM will yield a single major band of about 370 kDa on a denaturing polyacrylamide gel. The purity of compositions containing ATM can also be determined by amino-terminal amino acid sequence analysis.

Recombinant ATM may be purified by any suitable method, including but not limited to chromatography, precipitation, electrophoresis, and if desired, combinations of various methods. Chromatographic techniques suitable for ATM purification include ion exchange chromatography, affinity chromatography, size-exclusion, chromatography, using liquid chromatographic systems such as HPLC or gas chromatographic systems. ATM purification may be isolated by precipitation, for example immunoprecipitation using anti-ATM antibody, using calcium, or using an antibody against a "tag" group attached to ATM. Electrophoretic methods suitable for ATM purification include but are not limited to isoelectric focusing, polyacrylamide gel electrophoresis under nondenaturing or denaturing conditions, agarose gel electrophoresis, iontophoresis, or other electrophoretic methods of protein separation.

In one preferred embodiment, recombinant ATM is a fusion protein having a FLAG tag at the N-terminal end of the protein. In another preferred embodiment, recombinant ATM is a fusion protein having both FLAG and hexahistidine (HIS) tags located at the N-terminal end of the protein. HeLa cells were infected with ATM vaccinia virus for 32 hours and lysed to release ATM. Cytoplasmic extracts from cells infected with ATM-expressing virus were incubated in small batches with FLAG M2 affinity resin (Sigma), under suitable conditions to allow ATM to bind to the resin. FLAG-tagged ATM was eluted from the affinity resin by peptide competition using 1 mg/ml FLAG peptide (Sigma). Typical yields of substantially purified ATM were between 0.3–0.5 ug/ul of eluate from FLAG M2 resin. After elution, eluate was optionally concentrated using Microcon YM-100 centrifugal filter (Amicon). Western blot analysis using anti-ATM antibodies (FIG. 2) or anti-FLAG antibodies confirmed the presence of ATM in the eluate. Silver-stained protein showed that most of the protein present in the concentrated eluate was full-length ATM, although traces of smaller protein fragments at much lower concentrations were also detected (FIG. 3).

In accordance with one aspect of the present invention, high yields of ATM protein are produced using an expression system as disclosed herein, where ATM protein is preferably recovered in substantially purified form. Yields are greater than 2 ug substantially purified ATM from 300 grams of tissue, or greater than 1 ug substantially purified ATM from $8 \times 10^6$ cells. Preferably, yields of at least 2 ug, preferably 5 ug, even more preferably 10 ug, and even more preferably 20 ug or 25 ug or 30 ug or more substantially purified ATM is recovered from $8 \times 10^6$ infected cells. In some embodiments, approximately 500 ul FLAG M2 resin eluate is collected from about $25 \times 10^6$ infected HeLa cells at a concentration of about 0.4–0.5 mg protein/ml of eluate, giving a total yield of about 200–250 ug substantially pure ATM. In other embodiments, approximately 100 ul of FLAG M2 resin eluate is collected from $8 \times 10^6$ infected cells at a concentration of about 0.3–0.4 mg/ml of eluate, giving a total yield of about 75 ug of substantially pure ATM. One of skill in the art can optimize yield according to the infected host cells or tissue used, the equipment and reagents available, purification methods used, and degree of purity desired.

The present disclosure enables one of skill in the art to adapt the ATM expression system provided by the present invention, in order to purify recombinant ATM protein by any desired method. For example, expression vectors can be constructed to attach a glutathione-S-transferase (GST) tag to the ATM protein, and GST-tagged ATM can be affinity-purified. Further, one of skill in the art can carry out additional manipulations to recover ATM in the desired form. For example, a composition of substantially purified affinity-tagged ATM can be treated to remove the affinity tags, e.g., GST tags may be removed by proteolytic cleavage with enterokinase or thrombin. For ATM proteins having multiple tags, tags may be selectively removed if desired, e.g., a GST-and -FLAG-tagged ATM may be treated with thrombin to remove the GST tag, while the FLAG tag remains attached. Alternately, self-cleaving tags such as the intein system may be used to substantially purify ATM protein and then remove the affinity tag used for purification.

ATM Proteins and Functional Fragments

The invention includes functional ATM protein as well as functional fragments thereof. As used herein, the term "functional polypeptide" refers to a polypeptide that possesses biological function or activity which is identified through a defined functional assay and which is associated with a particular biologic, morphologic, or phenotypic alteration in the cell. The term "functional fragments of ATM" refers to all fragments of ATM having ATM activities including kinase activity against ATM substrates, autophosphorylation, binding to anti-ATM antibodies, effects on cell cycle and DNA damage repair, or phenotypic effects when expressed in cells, tissues, or whole organisms.

In accordance with one aspect of the invention, the kinase activity of ATM, whether as autophosphorylation or kinase activity against other substrates, can be utilized in bioassays to identify biologically active fragments of ATM or related polypeptides expressed according to the present disclosure. In addition, inhibitors of ATM can be used to inhibit ATM activity and cause loss of ATM function resulting in, for example, loss of the A-T phenotype at the cellular, tissue, or organismal level.

In accordance with another aspect of the invention, minor modifications of the ATM primary amino acid sequence can result in proteins or fragments which have substantially equivalent activity to the ATM protein described herein. Such modifications may be deliberate, as by site-directed mutagenesis, or may be spontaneous. All of the polypeptides produced by such ATM modifications are included herein as long as the peptide possesses some aspect of ATM biological activity as described in the present disclosure. One skilled in the art can determine which ATM biological activity or activities will be tested, depending on the intended use of the modified ATM protein or fragment.

In Vitro Kinase Assays

To test ATM function, an in vitro kinase assay using GST-p53 as the target substrate was performed. Reactions were carried out in the presence or absence of 10 µg of sheared salmon sperm DNA. Under certain reaction conditions, ATM in the presence of DNA with double-stranded breaks phosphorylated GST-p53, whereas ATM without DNA showed decreased kinase activity. Under other reaction conditions, ATM phosphorylation of p53 did not show DNA dependence. One of skill in the art can determine the suitable reactions for DNA-dependent and DNA-independent ATM phosphorylation of p53. Plasmid DNA, representing intact DNA, produced a low level of phosphorylation when preincubated with ATM. GST-p53 phosphorylation was inhibited after wortmannin pretreatment of ATM. Kinase reactions containing both DNA and DNase did not have phosphorylated GST-p53. Reactions lacking ATM showed no phosphorylation of p53 substrate.

In vitro kinase assays using PHAS-1 as a target showed similar phosphorylation levels between reactions containing DNA and those where DNA was not included. ATM activity was inhibited by wortmannin pretreatment.

Autophosphorylation of ATM

Under some reaction conditions, autophosphorylation of ATM occurs in a DNA-independent fashion. Unexpectedly, ATM autophosphorylation decreased in the presence of the GST-p53 substrate.

The present disclosure describes production and purification of functional ATM, preferably by overexpression of ATM, preferably using vaccinia virus as the expression system. Use of vaccinia virus permits expression in mammalian hosts, which can be advantageous when compared to the baculovirus expression system. Previous attempts to achieve ATM production in baculovirus were not successful (Ziv et al. (1997) *Oncogene* 159–167; Scott et al. (1998) *Biochem and Biophys Res Comm* 245: 144–148). The inability of insect cells to mass produce the large protein may be due to amino acid differences or lethal effects to the host due to large quantities of expressed protein. As exemplified by the present disclosure, use of mammalian hosts diminished the problem of rare codons. However, one of skill in the art could practice the viral expression method disclosed here using non-mammalian cells including insect cells, possibly by modifying codon usage in the ATM-encoding polynucleotide.

Cytoplasmic transcription is an especially advantageous property of the vaccinia virus with respect to aspects of the present invention. Transcription of viral RNA outside the host cell nucleus avoids the problem of incorrect RNA splicing. Given the large size of the ATM cDNA, this may be a problem in non-mammalian cells.

In accordance with aspects of the present invention, some recombinant ATM was found in the nucleus but the majority of the recombinant ATM protein was in the cytoplasm. This phenomenon may be due to oversaturation of the host nucleus with ATM, resulting in the presence of a large amount of cytoplasmic ATM. In vitro kinase assays demonstrated that altered localization of ATM does not interfere with activity. In a preferred embodiment, cytoplasmic recombinant ATM was purified in accordance with the methods of the present invention, and no steps to release nuclear ATM from lysates were performed. Methods for purifying recombinant ATM as described herein can be modified by one of skill in the art to include steps to release nuclear ATM.

Figure 2:
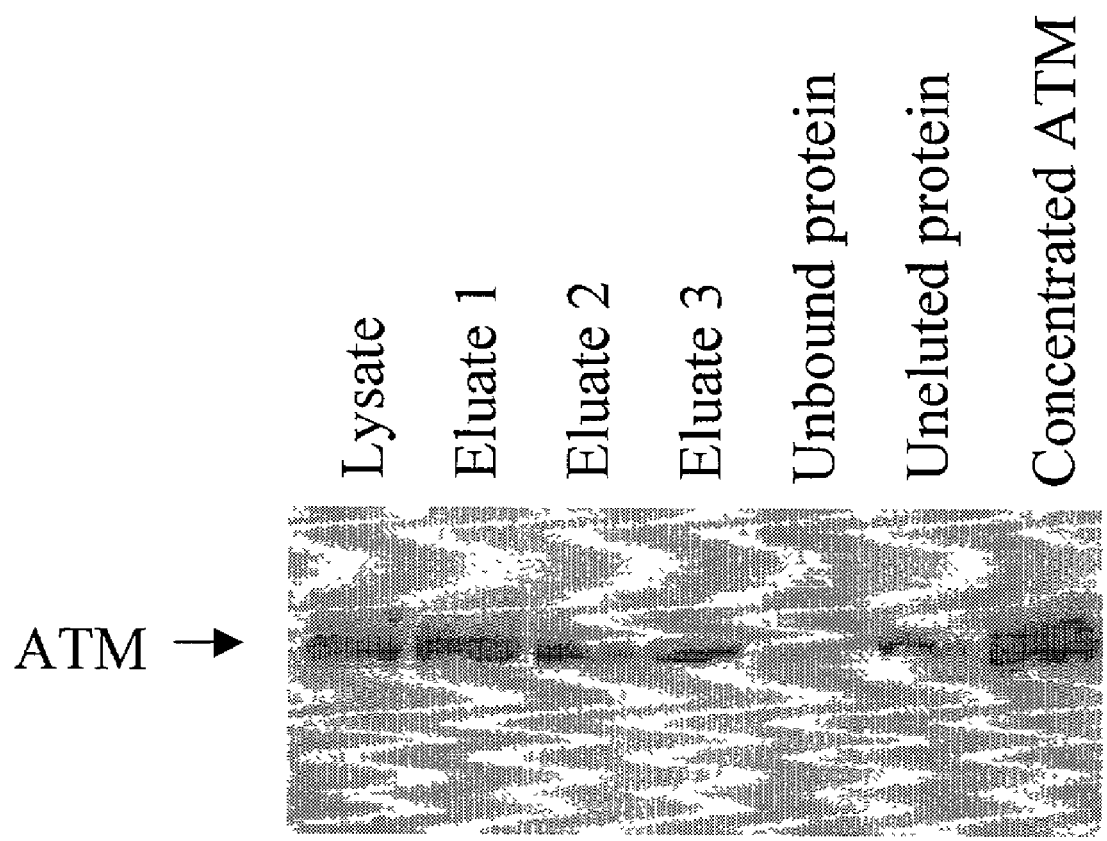
FIG. 2. Western blot showing purification of ATM using FLAG M2 affinity resin. HeLa cells were infected with ATM vaccinia virus for 32 hours, lysed, and ATM protein purified using affinity chromatography. Western blot analysis, using anti-ATM antibody, showed the presence of recombinant ATM in the indicated fractions from the purification process.

In accordance with one aspect of the invention, lysates of cells containing vaccinia virus expressing ATM contained proteins of varying lengths recognized by anti-ATM antibody, as can be seen in FIG. 1. Without wishing to be limited to this theory, the presence of varying sizes of ATM probably represent degradation of the full-length protein since viral invasion of host cells results in disruption of host cell cellular machinery and death. Thus, ATM degradation is possibly due to protease activity induced by the natural virus life cycle. The ATM degradation observed in cell lysates did not present a difficulty in ATM purification, as can be seen in FIGS. 2 and 3, showing that one ATM band of 370 kDa was obtained. Similarly, the decrease in p53 phosphorylation seen at later timepoints (FIG. 1, lower panel) was presumed to be due to substrate degradation and not loss of ATM function.

In one embodiment, purification of ATM was attempted using a hexahistidine (HIS) tag positioned N-terminal of ATM. Both nickel and cobalt resins were used to capture the recombinant protein but neither worked, probably due to steric obstruction of the interaction between the metal ion and HIS. In this embodiment, the HIS tag is positioned between the FLAG tag and ATM so it is possible that the HIS tag was inaccessible for binding to either resin. Use of various anti-FLAG antibodies to purify ATM showed that FLAG-M2 affinity resin gave better results than the FLAG M5 affinity resin, possibly due to the fact that calcium is necessary for binding between the M5 resin and FLAG epitope and the observation that ATM precipitates in the presence of calcium. When the eluate of a FLAG-M2 affinity resin was run on a denaturing polyacrylamide gel and silver stained, purified ATM was the major protein present in the eluate (FIG. 3)

Purified ATM was subjected to in vitro kinase assays to test for protein function, targeting either GST-p53 or PHAS-1 substrates. Under some reaction conditions ATM, in the presence of double-strand DNA breaks, may phosphorylate GST-p53, whereas reactions without DNA or DNA treated with DNase did not show p53 phosphorylation. In contrast, purified ATM, independent of DNA, phosphorylated PHAS-1. A DNA requirement for p53 phosphorylation suggests a mechanism for ATM recruitment for its involvement in DNA damage related pathways. In the absence of DNA breaks, ATM may have a more constitutive role, one that does not involve repair or checkpoint mechanisms. In the case of PHAS-1, a translation factor of insulin production, its interaction with ATM occurs constitutively, thereby not requiring the DNA dependency. The mechanism of DNA interaction with ATM, if any, is unclear because ATM has no obvious DNA binding domains or capabilities. Immediate upstream activation of ATM is not known. Our data suggest that DNA may serve as an agent to recruit ATM into particular pathways, initiating certain responses. Double stranded DNA breaks serve as a direct initiator of ATM activity upon p53 and perhaps other damage related proteins, whereas ATM DNA-independent activities occur with normal cellular mechanisms. ATM autophosphorylation is DNA independent and decreased in p53 phosphorylation reactions. Smith et al (1999) *Proc Natl Acad Sci USA* 96: 11134–11139) reported that ATM may form tetramers. It is proposed that autophosphorylation may occur when these complexes form, activating ATM in its constitutive roles.

Structural Analysis of ATM

In another aspect of the invention, structural analysis of substantially purified ATM protein provides a structure-based understanding of the function and uses of ATM protein. In one embodiment, purified ATM protein is analyzed using cryo-EM, for example using methods described in Chiu et al (1998, *Jnl Mol Biol* 284: 1075–1081). In another embodiment, naturally occurring domains are identified after partial protease digestion of substantially purified ATM, expression plasmids bearing these domains are constructed, and individual ATM domains are purified. Further embodiments include using structural analysis of individual ATM domains to collectively provide or predict ATM structure.

Expression and Screening of ATM Mutations

In accordance with another aspect of the present invention, expression and purification methods of the present invention can be carried out utilizing nucleotide sequences of all or part of the ATM gene having various mutations. For example, Shiloh et al., (U.S. Pat. No. 5,858,661), and Gatti et al. (U.S. Pat. No. 5,955,279) disclosed a series of mutations that produced the A-T disease phenotype, dominated by deletions and insertions, wherein smaller mutations of 12 nucleotides or less reflect sequence alterations in genomic DNA, and deletions spanning larger segments of the ATM transcript were found to reflect exon skipping and did not correspond to genomic deletions. Of the 44 mutations identified, 39 (89%) were expected to inactivate the ATM protein by truncating it, by abolishing correct initiation or termination of translation, or by deleting large segments. Additional mutations included four smaller in-frame deletions and insertions, and one substitution of a highly conserved amino acid at the PI 3-kinase domain. Shiloh et al. predicted that the profile of mutations causing the A-T was dominated by mutations expected to completely inactivate the ATM protein.

In one embodiment, recombinant ATM protein variants encoded by nucleic acid sequences having various mutations in the A-T gene (also known as the ATM gene) can be produced and substantially purified, providing material for studies of activity and structure of ATM variants. In another embodiment, techniques of the present invention can be employed to compare structure and activity of ATM variants with the phenotypes observed in individuals carrying each of the variants.

In a further embodiment, methods of the present invention can be used to produce ATM variants to screen for those variants having specific properties. In view of the pleiotropic nature of the ATM gene, the range of phenotypes associated with various ATM genotypes may be even broader, and include mild progressive conditions not always defined as clear clinical entities.

In another embodiment, screening ATM variants will reveal factors related to the molecular pathology associated with the ATM gene. The ATM gene leaves a great deal of room for mutations, as it encodes a large transcript and the variety of mutations identified so far indicates a rich mutation repertoire. Techniques of the present invention provide methods to screen ATM variants resulting from various ATM mutations, in order to determine structural characteristics involved in ATM activity and function. Screening of ATM variants encoded by nucleic acid sequences encoding the exon skipping observed in many patients provides methods for elucidating the relationship between ATM sequence, structure, activity, function, and the severity of disease phenotype observed.

Definitions

The ATM protein and other materials can advantageously be in isolated form. As used herein, the term "isolated" denotes that the material has been removed from its original environment. For example, a naturally-occurring polynucleotide or polypeptide present in a living animal is not isolated, but the same polynucleotide or polypeptide, separated from some or all of the coexisting materials in the natural system, is isolated.

It is also advantageous that the sequences and other materials comprising the invention be in purified form. The term "purified" does not require absolute purity; rather, it is intended as a relative definition. For purposes of clarity, the term "substantially purified" or "substantially pure" is used herein to indicate that absolute purity is not required. Purification of starting material or natural material means that the concentration of the substantially purified material is at least about 2, 5, 10, 100 or 1000 times its original concentration (for example), advantageously 0.01% by weight, preferably at least about 0.1% by weight. Purified preparations of about 0.5%, 1%, 5%, 10% and 20% by weight are also contemplated.

EXAMPLES

Example 1

ATM Expression and Function

Cell Culture and Irradiation

CV-1 tk-cells were maintained in DME (Hyclone) supplemented with 10% fetal calf serum (Hyclone). The cells were grown in a humidifying incubator at 37° C. with 5% $CO_2$. HeLa cells were maintained in DMEM (Cellgro) supplemented with 10% fetal bovine serum (Hyclone) and 1% penicillin/streptomycin/glutamine (Gibco BRL) and human lymphoblastoid cells, L3, were maintained in RPMI (Cellgro) supplemented with 10% fetal bovine serum and 1% penicillin/streptomycin/glutamine. The cells were grown in a humidifying incubator at 37° C. with 5% $CO_2$. Cells treated with irradiation were exposed to 2 Gy gamma radiation. Cells infected with vaccinia virus were returned to 37° C. after infection until lysis.

Construction of pSCAT Vector pFT-YZ5, a baculovirus construct containing the full-length ATM cDNA, was generously donated by Yosef Shiloh. Directly flanking the 5' end of the ATM coding sequence are sequences coding for the FLAG epitope and hexahistidine tags. Liberation of the entire ATM coding sequence, including the FLAG and HIS tags, was performed by a SalI and KpnI (New England Biolabs) double digestion, resulting in a 5' piece of ATM of 4 kb and a 3+ fragment of 5.7 kb. The 5' ATM fragment was inserted into the vaccinia vector pSC65 at the SalI and KpnI sites, producing pSC-5ATM. The 3' ATM piece was ligated into pSC-5ATM at KpnI and checked with restriction enzymes for insertion in the correction orientation. DNA sequence was performed to ensure the integrity of all ligation sites. The final construct, pSCAT, is approximately 16.6 kb. All plasmids were grown in MAX DH5 cells (Gibco BRL) at 30° C.

Construction of Recombinant ATM Vaccinia Virus

CV-1 tk-cells were infected with WR strain of vaccinia virus at an MOI=0.1 pfu/cell for 2 hours followed by transfection of pSCAT using lipofectin (Gibco BRL). After 48 hours, cells were collected, resuspended in 1 ml Optimem (Gibco BRL), sonicated, and plated at 10–2 to 10–4 dilutions on tk-cells plated on 6-well plates to undergo selection for recombinant virus. A first overlay containing Basal Medium Eagle (Gibco BRL), L-glutamine, 0.05 mg/ml 5-bromo-2-deoxyuridine, 5% fetal bovine serum, and 1% low melting point agarose (BRL), was placed 2 hours after infection. The second overlay, containing 5 ug/ml neutral red, 0.002% x-galactose (Fisher), Basal Medium Eagle, and 1% LMP agarose, was placed 48 hours after infection. Within 36 hours, blue plaques were picked with a Pasteur pipette and placed into 500 ul Optimen and sonicated. Repeated plaque selection was performed until a purified virus was obtained.

Immunoblot Analysis of Expression

Lysates were prepared using lysis buffer containing 50 mM Tris HCl pH 7.4, 150 mM NaCl, 2 mM EDTA, 0.2% Triton X-100, 0.3% NP-40, 5 ug aprotinin (Sigma), 5 ug leupeptin (Calbiochem) and ImM PMSF (Sigma), incubated on ice and cleared by centrifugation. Virally expressed ATM was prepared in a cytoplasmic extract and run on a 5% denaturing polyacrylamide gel. To observe p53 phosphorylation, sonication was used to prepare nuclear extracts followed by electrophoresis on a 6 or 7% denaturing gel. SDS-PAGE gels were transferred for 2 hours at 100V, incubated with anti-ATM (Novus), anti-FLAG M2 (Sigma), or anti-phospho-p53 serine 15 (Cell Signalling) antibodies. Protein were visualized using enhanced chemiluminesence (Amersham).

Immunoprecipation and In Vitro Kinase Assay

Lysates were prepared as previously described and brought to a final volume of 800 ul. 5 ug of FLAG M2 antibody (Sigma) was used to immunoprecipitate the recombinant ATM and captured with Protein G Plus beads (Santa Cruz Biotechnology). In vitro kinase assay was performed using 50 mM HEPES pH 7.5, 150 mM NaCl, 10 mM $MnCl_2$, 10 mM $MgCl_2$, 1 mM DTT plus protease inhibitors, and 2 ug GST-p53 (Santa Cruz Biotechnology) or PHAS-1 (Stratagene), in the presence or absence of 10 ug of sheared salmon sperm (Stratagene), and pre-incubated for 3 minutes on ice. Upon addition of 20 $\mu$Ci $\gamma$-$^{33}$P-ATP (3000 Ci/mmol, Perkin Elmer) and 6.7 $\mu$M ATP, the kinase reaction was incubated at 30° for 15 minutes and stopped with SDS sample buffer. The reaction was run on a 7% SDS-PAGE gel, dried, and exposed to film. For DNase treated reactions, 10U of DNase (Gibco BRL) was added to the corresponding samples followed by a 37° incubation of all samples for 15 minutes. Wortmannin (Sigma), at a final concentration of 5 mM, was incubated with ATM prior to ATP addition for 30 minutes at room temperature.

Example 2

Purification of Recombinant ATM

FLAG M2 affinity resin (Sigma) was washed several times with lysis buffer. Approximately 25×10$^6$ HeLa cells were infected with recombinant vaccinia virus at MOI=5 pfu for 32 hours. Cells were lysed with 2 ml lysis buffer, incubated for 15 minutes on ice, and cleared by centrifugation. Cytoplasmic protein was incubated with 400 ul packed FLAG M2 affinity resin for 2 hours on rocker. Resin was collected by centrifugation for 2 minutes at 8000 rpm and washed with lysis buffer. 1 mg/ml FLAG peptide (Sigma) eluted ATM by peptide competition when incubated on rocker for 1 hr. Eluates were concentrated using a Microcon YM-100 centrifugal filter (Amicon). Final concentration of substantially purified ATM was typically between 0.3 to 0.5 mg/ml in the eluate. All purification steps were performed at 4° C.

Example 3

Activity of Purified ATM

Activity of substantially purified ATM protein was measured using an in vitro kinase assay. The assay contained ATM from Example 2 in the presence of 50 mM HEPES pH 7.5, 150 mM NaCl, 10 mM $MnCl_2$, 10 mM $MgCl_2$, 1 mM DTT plus protease inhibitors, and 2 ug GST-p53 (Santa Cruz Biotechnology) or PHAS-1 (Stratagene), in the presence or absence of 10 ug of sheared salmon sperm (Stratagene), and was preincubated for 3 minutes on ice. Upon addition of 20 $\mu$Ci $\gamma$-$^{33}$P-ATP (3000 Ci/mmol, Perkin Elmer) and 6.7 $\mu$M ATP, the kinase reaction was incubated at 30° for 15 minutes and stopped with SDS sample buffer. The reaction was run on a 7% SDS-PAGE gel, dried, and exposed to film. For DNase treated reactions, 10 units of DNase (Gibco BRL) was added to the corresponding samples followed by a 37° incubation of all samples for 15 minutes. Wortmannin (Sigma), at a final concentration of 5 mM, was incubated with ATM prior to ATP addition for 30 minutes at room temperature.

Although the invention has been described with reference to embodiments and examples, it should be understood that various modifications can be made without departing from the spirit of the invention. Accordingly, the invention is limited only by the following claims.

What is claimed is:

1. A method for recombinantly producing functional ataxia-telangiectasia (ATM) protein, comprising:
   providing a viral vector comprising a cDNA encoding the ATM protein operably linked to a promoter;
   infecting ATM deficient mammalian L3 cells with said viral vector, wherein said mammalian L3 cells are thereby made to produce functional ATM protein; and
   isolating said functional ATM protein produced by said mammalian L3 cells.

2. The method of claim 1, wherein said viral vector comprising a cDNA encoding the ATM protein operably linked to a promoter is a vaccinia viral vector.

3. The method of claim 1, wherein said promoter is a synthetic early/late viral promoter.

4. The method of claim 1, further wherein said ATM-deficient mammalian L3 cells producing said functional ATM protein exhibit regain of ATM function.

5. The method of claim 1 wherein isolating said functional ATM protein comprises binding an anti-ATM antibody to said ATM protein.

6. The method of claim 1, where said cDNA encoding the ATM protein is modified to comprise a FLAG epitope.

7. The method of claim 6, wherein isolating said functional ATM protein comprises binding an antibody specific for the FLAG epitope to said ATM protein.

8. The method of claim 1, further wherein said functional ATM protein is capable of phosphorylating ATM substrates.

9. The method of claim 8, wherein said substrates comprise p53 and PHAS-1.

10. A method for recombinantly producing functional ataxia-telangiectasia (ATM) protein, comprising:
    providing a vaccinia viral vector comprising a cDNA encoding the ATM protein operably linked to a promoter;
    infecting HeLa cells with said vaccinia viral vector, wherein said HeLa cells are made to express said cDNA and thereby produce functional ATM protein; and isolating said functional ATM protein produced by said HeLa cells.

11. The method of claim 10, wherein said promoter is a synthetic early/late viral promoter.

12. The method of claim 10 wherein isolating said functional ATM protein comprises binding an anti-ATM antibody to said ATM protein.

13. The method of claim 10, where said cDNA encoding the ATM protein is modified to comprise a FLAG epitope.

14. The method of claim 13, wherein isolating said functional ATM protein comprises binding an antibody specific for the FLAG epitope to said ATM protein.

15. The method of claim 10, wherein said functional ATM protein is capable of phosphorylating ATM substrates.

16. The method of claim 15, wherein said substrates comprise p53 and PHAS-1.

* * * * *